United States Patent [19]

Keifer et al.

[11] Patent Number: 5,229,501
[45] Date of Patent: Jul. 20, 1993

[54] EXPRESSION AND USE OF HUMAN FIBROBLAST GROWTH FACTOR RECEPTOR

[75] Inventors: Michael C. Keifer, Clayton; Pablo D. T. Valenzuela, Berkeley; Philip J. Barr, Oakland, all of Calif.

[73] Assignee: Chiron Corporation, Emeryville, Calif.

[21] Appl. No.: 640,029

[22] Filed: Jan. 11, 1991

[51] Int. Cl.5 ............................................. C07K 13/00
[52] U.S. Cl. .................................................... 530/399
[58] Field of Search .............................. 530/399, 350

[56] References Cited

PUBLICATIONS

Kiefer et al 1991 Growth Factors 5:115–127.
Isacchi et al 1990 Nuc. Acids Res. 18:1906.

Primary Examiner—Robert J. Hill, Jr.
Assistant Examiner—K. Carlson
Attorney, Agent, or Firm—Grant D. Green; Roberta L. Robins; Barbara G. McClung

[57] ABSTRACT

A new receptor for fibroblast growth factor has been cloned and expressed. The recombinant receptor is useful for inhibiting FGF activity, and for screening compounds for binding activity similar to that of FGF. A soluble, truncated recombinant receptor is also prepared, and is capable of binding FGF.

3 Claims, 2 Drawing Sheets

```
      P4         P1                                                           1
1 MWSWKCLLFWAVLVTATLCTARPSPTLPEQAQPWGAPVEVESFLVHPGDLLQLRCRLRDDVQSINWLRDGVQLAE   75
2 MWSWKCLLFWAVLVTATLCTARPSPTLPEQAQPWGAPVEVESFLVHPGDLLQLRCRLRDDVQSINWLRDGVQLAE   75
3 MWSWKCLLFWAVLVTATLCTARPSPTLPEQ---------------------------------------------   30
4 MWSWKCLLFWAVLVTATLCTARPSPTLPEQ---------------------------------------------   30
5 MWSWKCLLFWAVLVTATLCTARPSPTLPEQ---------------------------------------------   30
6 MWSWKCLLFWAVLVTATLCTARPSPTLPEQ---------------------------------------------   30

ARR
  SNRTRITGEEVEVQDSVPADSGLYACVTSSPSGSDTTYFSVNVSDALPSSEDDDDDDDSSSEEKETDNTKPN--P  148
  SNRTRITGEEVEVQDSVPADSGLYACVTSSPSGSDTTYFSVNVSDALPSSEDDDDDDDSSSEEKETDNTKPNRMP  150
  -----------------------------------------DALPSSEDDDDDDDSSSEEKETDNTKPN--P    59
  -----------------------------------------DALPSSEDDDDDDDSSSEEKETDNTKPNRMP    61
  -----------------------------------------DALPSSEDDDDDDDSSSEEKETDNTKPN--P    59
  -----------------------------------------DALPSSEDDDDDDDSSSEEKETDNTKPNRMP    61
                                                                  2
  VAPYWTSPEKMEKKLHAVPAAKTVKFKCPSSGTPNPTLRWLKNGKEFKPDHRIGGYKVRYATWSIIMDSVVPSDK  223
  VAPYWTSPEKMEKKLHAVPAAKTVKFKCPSSGTPNPTLRWLKNGKEFKPDHRIGGYKVRYATWSIIMDSVVPSDK  225
  VAPYWTSPEKMEKKLHAVPAAKTVKFKCPSSGTPNPTLRWLENGKEFKPDHRIGGYKVRYATWSIIMDSVVPSDK  134
  VAPYWTSPEKMEKKLHAVPAAKTVKFKCPSSGTPNPTLRWLKNGKEFKPDHRIGGYKVRYATWSIIMDSVVPSDK  136
  VAPYWTSPEKMEKKLHAVPAAKTVKFKCPSSGTPNPTLRWLKNGKEFKPDHRIGGYKVRYATWSIIMDSVVPSDK  134
  VAPYWTSPEKMEKKLHAVPAAKTVKFKCPSSGTPNPTLRWLKNGKEFKPDHRIGGYKVRYATWSIIMDSVVPSDK  136
         P2                                                 3
  GNYTCIVENEYGSINHTYQLDVVERSPHRPILQAGLPANKTVALGSNVEFMCKVYSDPQPHIQWLKHIEVNGSKI  298
  GNYTCIVENEYGSINHTYQLDVVERSPHRPILQAGLPANKTVALGSNVEFMCKVYSDPQPHIQWLKHIEVNGSKI  300
  GNYTCIVENEYGSINHTYQLDVVERSPHRPILQAGLPANKTVALGSNVEFMCKVYSDPQPHIQWLKHIEVNGSKI  209
  GNYTCIVENEYGSINHTYQLDVVERSPHRPILQAGLPANKTVALGSNVEFMCKVYSDPQPHIQWLKHIEVNGSKI  211
  GNYTCIVENEYGSINHTYQLDVVERSPHRPILQAGLPANKTVALGSNVEFMCKVYSDPQPHIQWLKHIEVNGSKI  209
  GNYTCIVENEYGSINHTYQLDVVERSPHRPILQAGLPANKTVALGSNVEFMCKVYSDPQPHIQWLKHIEVNGSKI  211
                                                                         P3
  GPDNLPYVQILKTAGVNTTDKEMEVLHLRNVSFEDAGEYTCLAGNSIGLSHHSAWLTVLEALEERPAVMTSPLYL  373
  GPDNLPYVQILKTAGVNTTDKEMEVLHLRNVSFEDAGEYTCLAGNSIGLSHHSAWLTVLEALEERPAVMTSPLYL  375
  GPDNLPYVQILKTAGVNTTDKEMEVLHLRNVSFEDAGEYTCLAGNSIGLSHHSAWLTVLEALEERPAVMTSPLYL  284
  GPDNLPYVQILKTAGVNTTDKEMEVLHLRNVSFEDAGEYTCLAGNSIGLSHHSAWLTVLEALEERPAVMTSPLYL  286
  GPDNLPYVQILKVIMAPVFVGQSTGKETTVSGAQVPVGRLSCPRMGSFLTLQAHTIHLSRDLATSRTSNRGHKV   284
  GPDNLPYVQILKVIMAPVFVGQSTGKETTVSGAQVPVGRLSCPRMGSFLTLQAHTIHLSRDLATSRTSNRGHKV   286
  TM
  EIIIYCTGAFLISCMVGSVIVYKMKSGTKKSDFHSQMAVHKLAKSIPLRRQVTVSADSSASMNSGVLLVRPSRLS  448
  EIIIYCTGAFLISCMVGSVIVYKMKSGTKKSDFHSQMAVHKLAKSIPLRRQVTVSADSSASMNSGVLLVRPSRLS  450
  EIIIYCTGAFLISCMVGSVIVYKMKSGTKKSDFHSQMAVHKLAKSIPLRRQVTVSADSSASMNSGVLLVRPSRLS  359
  EIIIYCTGAFLISCMVGSVIVYKMKSGTKKSDFHSQMAVHKLAKSIPLRRQVTVSADSSASMNSGVLLVRPSRLS  361
  EVSWEQRAAGMGGAGL*                                                           300
  EVSWEQRAAGMGGAGL*                                                           302
                                                      TK
  SSGTPMLAGVSEYELPEDPRWELPRDRLVLGKPLGEGCFGQVVLAEAIGLDKDKPNRVTKVAVKMLKSDATEKDL  523
  SSGTPMLAGVSEYELPEDPRWELPRDRLVLGKPLGEGCFGQVVLAEAIGLDKDKPNRVTKVAVKMLKSDATEKDL  525
  SSGTPMLAGVSEYELPEDPRWELPRDRLVLGKPLGEGCFGQVVLAEAIGLDKDKPNRVTKVAVKMLKSDATEKDL  434
  SSGTPMLAGVSEYELPEDPRWELPRDRLVLGKPLGEGCFGQVVLAEAIGLDKDKPNRVTKVAVKMLKSDATEKDL  436

SDLISEMEMMKMIGKHKNIINLLGACTQDGPLYVIVEYASKGNLREYLQARRPPGLEYCYNPSHNPEEQLSSKDL  598
  SDLISEMEMMKMIGKHKNIINLLGACTQDGPLYVIVEYASKGNLREYLQARRPPGLEYCYNPSHNPEEQLSSKDL  600
  SDLISEMEMMKMIGKHKNIINLLGACTQDGPLYVIVEYASKGNLREYLQARRPPGLEYCYNPSHNPEEQLSSKDL  509
  SDLISEMEMMKMIGKHKNIINLLGACTQDGPLYVIVEYASKGNLREYLQARRPPGLEYCYNPSHNPEEQLSSKDL  511

VSCAYQVARGMEYLASKKCIHRDLAARNVLVTEDNVMKIADFGLARDIHHIDYYKKTTNGRLPVKWMAPEALFDR  673
  VSCAYQVARGMEYLASKKCIHRDLAARNVLVTEDNVMKIADFGLARDIHHIDYYKKTTNGRLPVKWMAPEALFDR  675
  VSCAYQVARGMEYLASKKCIHRDLAARNVLVTEDNVMKIADFGLARDIHHIDYYKKTTNGRLPVKWMAPEALFDR  584
  VSCAYQVARGMEYLASKKCIHRDLAARNVLVTEDNVMKIADFGLARDIHHIDYYKKTTNGRLPVKWMAPEALFDR  586
                                TK
  IYTHQSDVWSFGVLLWEIFTLGGSPYPGVPVEELFKLLKEGHRMDKPSNCTNELYMMMRDCWHAVPSQRPTFKQL  748
  IYTHQSDVWSFGVLLWEIFTLGGSPYPGVPVEELFKLLKEGHRMDKPSNCTNELYMMMRDCWHAVPSQRPTFKQL  750
  IYTHQSDVWSFGVLLWEIFTLGGSPYPGVPVEELFKLLKEGHRMDKPSNCTNELYMMMRDCWHAVPSQRPTFKQL  659
  IYTHQSDVWSFGVLLWEIFTLGGSPYPGVPVEELFKLLKEGHRMDKPSNCTNELYMMMRDCWHAVPSQRPTFKQL  661

VEDLDRIVALTSNQEYLDLSMPLDQYSPSFPDTRSSTCSSGEDSVFSHEPLPEEPCLPRHPAQLANGGLKRR*   820
  VEDLDRIVALTSNQEYLDLSMPLDQYSPSFPDTRSSTCSSGEDSVFSHEPLPEEPCLPRHPAQLANEGLKRR*   822
  VEDLDRIVALTSNQEYLDLSMPLDQYSPSFPDTRSSTCSSGEDSVFSHEPLPEEPCLPRHPAQLANGGLKRR*   731
  VEDLDRIVALTSNQEYLDLSMPLDQYSPSFPDTRSSTCSSGEDSVFSHEPLPEEPCLPRHPAQLANGGLKRR*   733
```

FIG. 2

EXPRESSION AND USE OF HUMAN FIBROBLAST GROWTH FACTOR RECEPTOR

TECHNICAL FIELD

This invention relates to the fields of molecular biology and pharmaceutical research. More specifically, this invention relates to the recombinant expression of a human high-affinity fibroblast growth factor (FGF) receptor, and its use in combination with glycosaminoglycans to model compounds capable of mimicking FGF binding.

BACKGROUND OF THE INVENTION

The fibroblast growth factors (FGFs) are a family of structurally related polypeptides that regulate the growth and differentiation of a diverse number of cell types. Acidic and basic FGFs are mitogenic for cell types of mesenchymal, epithelial and neural origin (K. Thomas, FASEB J (1987) 1:434-440; D. Gospodarowicz, Meth Enzymol (1987) 147:106-119). The more recently discovered members of the FGF family have been implicated in early developmental processes and in epithelial cell growth and maintenance (R. Moore et al, EMBO J (1986) 5:919-924; A. Jakobovits et al, Proc Natl Acad Sci USA (1986) 83:7806-7810; P. W. Finch et al, Science (1989) 245:752-755). Currently, the FGF family consists of seven distinct gene products including acidic and basic FGFs (M. Jaye et al, Science (1986) 233:541-545; J. A. Abraham et al, Science (1986) 233:545-548; J. A. Abraham et al, EMBO J (1986) 5:2523-2528), Jakobovits et al, supra), a growth factor identified from Kaposi's sarcoma DNA (hst-1 or KS-FGF) (P. D. Bovi et al, Cell (1987) 50:729-737; M. Taira et al, Proc Natl Acad Sci USA (1987) 84:2980-2984), FGF-5 (X. Zhan et al, Mol Cell Biol (1988) 8:3487-3495), FGF-6 (I. Marics et al, Oncogene (1989) 4:335-340) and keratinocyte growth factor, KGF or FGF-7 (P. W. Finch et al, supra).

The large number of FGFs and their diverse spectrum of activities suggests that several receptors may mediate their effects on cells. Indeed, for the acidic and basic FGFs themselves, two classes of receptors have been well documented which are distinguished by their affinities for FGF. For example, the binding of bFGF to a high affinity site on baby hamster kidney (BHK) cells occurs with a dissociation constant in the 20 pM range, whereas bFGF binding to the low affinity site occurs with a dissociation constant in the 2 nM range, and is released with 2 M NaCl. The FGF receptor has been implicated as the entry portal for Herpes simplex virus (HSV). Several high affinity FGF receptor cDNAs have been cloned (P. L. Lee et al, Science (1989) 245:57-60; E. Pasquale & S. J. Singer, Proc Natl Acad Sci USA (1989) 86:5449-5453; M. Ruta et al, Oncogene (1988) 3:9-15; H. H. Reid et al, Proc Natl Acad Sci USA (1990) 87:1596-1600; A. Isacchi et al, Nuc Acids Res (1990) 18:1906; D. E. Johnson et al, Mol Cell Biol (1990) 10:4728-4736) and shown by structural homology to be members of the cell surface protein-tyrosine kinase family of proteins. This group of membrane-bound proteins are thought to play an important role in the regulation of cell growth. They include the receptors for epidermal growth factor, platelet-derived growth factor, colony stimulating factor-1, insulin, and insulin-like growth factor-1 (for recent review see A. Ullrich & J. Schlessinger, Cell (1990) 61:203-212).

Structural analyses of the extracellular regions of the chicken FGF receptor cDNA suggests that the FGF receptors also belong to the immunoglobulin supergene family (P. L. Lee et al, supra). Accordingly, Reid et al, (supra) have found several forms of the bFGF receptor mRNA in developing mouse brain that contain either two or three immunoglobulin-like domains. Moreover, they detected a region of sequence variability between the first and second immunoglobulin-like domains. In this case, amino acids 148 and 149 are sometimes deleted in the predicted sequences for proteins that contain 2 immunoglobulin-like domains. Recently, four forms of the cDNA encoding the human two immunoglobulin-like domain FGF receptor have been identified (D. E. Johnson et al, supra). Two of these forms are homologous to the mouse two immunoglobulin-like domain FGF receptor in that they vary at amino acids 148 and 149 (H. H. Reid et al, supra). While the other two forms of the human FGF receptor also vary at these amino acids, they are unique in that they lack a transmembrane domain and the cytoplasmic tyrosine kinase domain. More recently, a fifth form of the human FGF receptor cDNA has also been isolated (A. Isacchi et al, supra), and is homologous to the mouse three immunoglobulin-like-domain FGF receptor. In addition to the five forms of the FGF receptor, Southern blot analysis and the cloning of two related cDNAs, bek (H. H. Reid et al, supra; S. Kornbluth et al, Mol Cell Biol (1988) 8:5541-5544) and a bek-related molecule (H. H. Reid et al, supra), indicate that FGF receptors are members of a multigene family.

A number of researchers have recently reported expression of various FGF receptors. See R. J. Kaner et al, Science (1990) 248:1410-13; A. Mansukhani et al, Proc Nat Acad Sci USA (1990) 87:4378-82; C. A. Dionne et al, EMBO J (1990) 9:2685-92; and D. P. Mirda & L. T williams, Clin Res (1990) 38:310A. However, the reported experiments in general do not disclose the expression of human FGF receptor in quantity sufficient for study.

In order to usefully study the binding of FGF analogs to the FGF receptor, one must have available sufficient quantities of active receptor for study. Further, the receptor must be in a useful form.

DISCLOSURE OF THE INVENTION

A new human FGF receptor has now been cloned and expressed using cDNA obtained from a human liver cell line. The expression of high levels of the extracellular region of this FGF receptor in a baculovirus-/insect cell system yields a high affinity FGF-binding protein that is active in radioreceptor assays, inhibits cell growth and that can be used to study the ligand-receptor interaction. Furthermore, four forms of the cDNAs that encode the FGF receptor have now been identified in several tissues and cell lines, suggesting there exists an extensive distribution of alternate forms that are generated by differential RNA splicing.

Thus, one aspect of the invention is a recombinant FGF receptor (rFGF-R), which is capable of binding aFGF and/or bFGF. Another aspect of the invention is a recombinant fragment of FGF-R comprising the extracellular domain (soluble FGF-R, or "sFGF-R"), which is capable of binding aFGF and/or bFGF.

Another aspect of the invention is a method for detecting FGF in a sample, by employing rFGF-R in a manner analogous to an anti-FGF antibody in any form of immunoassay. For example, one may detect FGF by providing a support comprising rFGF-R bound to a solid surface, contacting the support with a sample to be assayed for FGF, removing the portion of the sample which does not bind to the support, and detecting the presence of bound FGF on the support (e.g., by using a labeled anti-FGF antibody, by competition with labeled FGF, etc.).

Another aspect of the invention is a method for inhibiting the activity of FGF, using rFGF-R. Thus, rFGF-R may be used to inhibit FGF-mediated activities. For example, one method of the invention is the inhibition of FGF-dependent tumor growth by administering an effective amount of sFGF-R. Another method of the invention is the method of inhibiting angiogenesis (e.g., of a tumor) by administering an effective amount of sFGF-R. Another method of the invention is the method of inhibiting FGF-dependent cell growth in vitro by administering rFGF-R.

Another aspect of the invention is the use of rFGF-R to screen and identify compounds which mimic FGF binding. Compounds identified in this manner may be agonists or antagonists. Agonists are useful in situations in which FGF activity is beneficial, e.g., for acceleration of wound healing, nerve outgrowth, and the like. Antagonists are useful for inhibiting the activity of FGF, for example, to inhibit the growth of FGF-dependent malignancies, and the like. Compounds may be screened by providing a support having bound rFGF-R, contacting the support with a candidate compound, and detecting any compound bound to the support. Suitable compounds may also be used to block or inhibit binding by Herpes virus.

BRIEF DESCRIPTION OF THE DRAWINGS

FIG. 2 depicts an amino acid sequence comparison of the six different human FGF receptor forms. Sequences have been aligned for maximum identity and those that differ or are deleted have been boxed. Various domains (abbreviations as in FIG. 1) and regions used for PCR primers (P1-P4) are indicated above sequence 1 (flg 5). The putative signal peptidase cleavage site is also indicated (↓). Sequence 2 was from A. Isacchi et al, supra and sequences 3-6 were from D. E. Johnson et al, supra.

MODES OF CARRYING OUT THE INVENTION

A. Definitions

Figure 1:
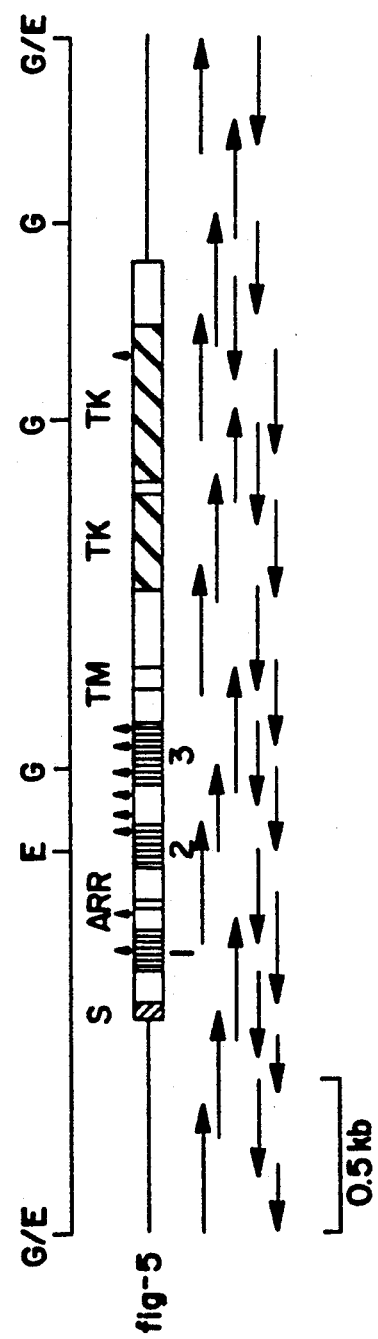
FIG. 1 depicts a schematic diagram of the human FGF receptor cDNA (FIG. 5) and sequencing strategy. The translated regions are boxed, and various shaded domains are indicated: S, signal peptide; 1-3, immunoglobulinlike-domains 1-3; ARR, acidic amino acid rich region; TM, transmembrane region; TK, tyrosine kinase domains. Potential Asn-linked glycosylation sites are also indicated (♦) as are the BglII (G) and EcoRI (E) restriction endonuclease sites. Although shown, the location of the most carboxyl-terminal consensus glycosylation site most likely precludes its use. Sequences were obtained by using M13 primers and specific internal primers. Arrows indicate the direction and extent of individual sequencing runs. The DNA sequence is in the Genbank and EMBL data bases, and accession numbers are available from these organizations.

The term "FGF receptor" or "FGF-R" as used herein refers to the human FGF receptor or a fragment thereof capable of binding FGF in the presence of heparin, and having an amino acid sequence substantially as depicted in FIG. 2. The term "rFGF-R" refers to active FGF-R prepared by recombinant means. A preferred form of rFGF-R is soluble rFGF-R ("sFGF-R"), which is a truncated form obtained by expressing only the extracellular domain. It is surprisingly found that the truncated form retains its FGF-binding activity, and thus may be used to assay compounds for FGF-like binding activity or to bind actual FGF and thus inhibit its activity. The preferred sFGF-R of the invention is a 58 kDa glycoprotein which binds bFGF with a $K_d$ of 2-5 nM.

The term "substantially pure" indicates a protein or composition that is essentially free of contaminants similar to the protein. In the present case, the normal contaminants associated with FGF-R predominately include human proteins. Thus, rFGF-R is substantially pure if it is essentially free of human proteins. "Essentially free" is determined by weight. In general, a composition containing 70% rFGF-R and $\leq$30% human proteins may be considered substantially pure. Preferably, the composition will be at least 80% rFGF-R, more preferably at least 90%, and most preferably $\geq$95% rFGF-R. The presence of dissimilar components does not affect the determination of purity, thus a composition containing 0.7 mg/mL rFGF-R in PBS will still be considered substantially pure if it contains $\leq$0.3 mg/mL other human proteins.

The term "effective amount" refers to an amount of rFGF-R sufficient to exhibit a detectable therapeutic effect. The therapeutic effect may include, for example, without limitation, inhibiting the growth of undesired tissue or malignant cells, inhibiting the growth of FGF-dependent cells in the presence of cells not so constrained, inhibiting infection by HSV, and the like. The precise effective amount for a subject will depend upon the subject's size and health, the nature and severity of the condition to be treated, and the like. Thus, it is not possible to specify an exact effective amount in advance. However, the effective amount for a given situation can be determined by routine experimentation based on the information provided herein.

The term "specific binding" indicates binding which defines a generally stoichiometric ligand-receptor relationship. Specific binding indicates a binding interaction having a low dissociation constant, which distinguishes specific binding from non-specific (background) binding.

"PCR" refers to the technique of polymerase chain reaction as described in Saiki, et al., Nature 324:163 (1986); U.S. Pat. No. 4,683,195; and U.S. Pat. No. 4,683,202.

B. General Method

The FGF-R may be cloned and expressed as described below, based on the disclosed PCR primer sequences. It is presently preferred to express rFGF-R using a baculovirus vector, see, e.g., commercially available kits from Invitrogen, San Diego CA ("Max-Bac" kit), Summers and Smith, *Texas Agricultural Experiment Station Bulletin No.* 1555 (1987). Although other expression systems are not excluded, see, e.g., Sambrook et al., *Molecular Cloning: A Laboratory Manual*, Cold Spring Harbor Laboratory Press, Cold Spring Harbor N.Y., 1989 (bacterial expression); Barr et al., *Yeast Genetic Engineering*, Butterworths, Boston, Mass., 1989 (yeast expression); U.S. Pat. Nos. 4,399,216; 4,912,040; 4,740,461; 4,959,455 (these patents are incorporated herein by reference) (mammalian cell expression).

Using a baculovirus expression system, the protein is expressed as a glycoprotein in insect cells, and may easily be purified using lentil lectin chromatography. Active truncated forms of rFGF-R may be prepared by expressing only the extracellular binding domain, preferably aa$_{1-374}$.

Immunoassay protocols may be based, for example, upon competition, direct reaction, or sandwich type assays. Protocols may also use solid supports, or may involve immunoprecipitation. Most assays involve the use of labeled antibody or ligand. The labels may be, for example, fluorescent, chemiluminescent, radioactive, dye molecules, or enzymes. Assays that amplify the signals from the probe are also known, for example, assays that utilize biotin and avidin, and enzyme-labeled and mediated immunoassays, such as ELISA assays.

Typically, an assay for detecting FGF or FGF analogs will involve selecting and preparing the test sample, such as a biological sample, and then incubating it with the FGF-R under conditions that allow receptor-ligand complexes to form. Such conditions are well known in the art. In a heterogeneous format, the receptor is bound to a solid support to facilitate separation of the sample from the receptor after incubation. Examples of solid supports that can be used are nitrocellulose, in membrane or microtiter well form; polyvinylchloride, in sheets or microtiter wells; polystyrene latex, in beads or microtiter plates; polyvinylidine fluoride, known as Immobulon TM; diazotized paper; nylon membranes; activated beads; and Protein A beads. The solid support is typically washed after separating it from the test sample. In a homogeneous format, the test sample is incubated with a soluble form of the receptor in solution (e.g., sFGF-R), under conditions that will precipitate any receptor-ligand complexes that are formed, as is practiced in the art. The precipitated complexes are then separated from the test sample, for example, by centrifugation.

The complexes formed comprising FGF or FGF analogs in either the homogenous or heterogenous format can be detected by any of a number of techniques. Depending on the format, the complexes can be detected with labeled antibodies against FGF-receptor, FGF, or FGF analogs; or labeled FGF-R or, if a competitive format is used, by measuring the amount of bound, labeled competing FGF or FGF analogs.

The use of enzyme-linked antibodies is one well-known method for detecting receptor-ligand complexes. This method depends upon conjugation of an enzyme to antibodies against FGF, FGF analogs, or FGF-R, and uses the bound enzyme activity as a quantitative label. Enzymes suitable for labeling are known in the art, and include, for example, horseradish peroxidase and urease. Enzyme activity, bound to the receptor-ligand complex, is measured by adding the specific enzyme substrate, and determining product formation or substrate utilization. For ease, the substrate can be chosen so that substrate utilization can be determined colorimetrically.

Kits suitable for FGF or FGF analog detection can contain the appropriate reagents, which may or may not be labeled, such as FGF-R, FGF, or FGF analogs, or antibodies directed against FGF-R, FGF, or FGF analogs in suitable containers; along with the remaining reagents and materials required for the conduct of the assay (e.g., wash buffers, detection means, such as labeled FGF or FGF analogs or labeled anti-FGF-R), as well as a suitable set of assay instructions.

It is convenient to use sFGF-R to assay compounds for FGF-like binding activity, and thus to identify compounds which may serve as agonists or antagonists. In a typical screening assay, sFGF-R is adsorbed onto a support (such as the wells of a microtiter plate), fixing with glutaraldehyde if necessary. Alternatively, the sFGF-R may be immobilized using a lectin, such as ConA. The support is then contacted with a solution containing the compound(s) in question, allowed to incubate, and the remaining solution removed. After several washes, the plate is examined for the presence of bound compound. Bound compound may be detected by spectroscopic means (for example colorimetric or fluorometric means, depending on the characteristics of the compound), or by radioactive means if the compound has been so labeled. Alternatively, one may assay the compound for competition with labeled FGF. A large number of such assays can be performed and analyzed simultaneously, for example by conducting the experiments in an array (e.g., using a microtiter dish). In order to more completely model FGF, the compounds should be assayed for binding in the presence of heparin. It is theorized that both low affinity and high affinity FGF receptors are required for full FGF activity in vivo. It has now been found that FGF fails to bind the high affinity receptor with the same affinity in the absence of the low affinity receptor, but that the presence of sufficient heparin restores binding. Thus, one may completely model the FGF binding system in vitro using only sFGF-R and heparin. Compounds which exhibit a high affinity for sFGF-R may then be assayed for biological activity against FGF-R, or for inhibition of HSV infectivity, in an appropriate whole cell assay.

FGF is known to stimulate the growth and proliferation of many cell types, including normal cells of mesenchymal, epithelial or neural origin, and tumor cells, including melanoma. Some tumor types depend upon autocrine activity of FGF for proliferation. Accordingly, it is possible to employ rFGF-R to inhibit such proliferation in vivo or in vitro. In vivo, one may administer an effective amount of rFGF-R, preferably sFGF-R, to inhibit the undesirable growth of normal tissue (e.g., in scar formation, psoriasis, and other hyperplasias) or malignant tissue (as in the case of tumors, carcinomas, and the like). As FGF may stimulate angiogenesis, administration of rFGF-R may be used, for example, to inhibit the vascularization of inoperable tumors.

HSV is believed to invade susceptible cells through the FGF receptor. Thus, one may inhibit HSV infection by administering sFGF-R to susceptible surfaces, for example the mucosal membranes. Such administration is preferably in the form of a lotion, ointment, salve, or aerosol.

Compositions of the invention for administration will generally include an effective amount of sFGF-R in addition to a pharmaceutically acceptable excipient. Suitable excipients include most carriers approved for oral or parenteral administration, including water, saline, Ringer's solution, Hank's solution, and solutions of glucose, lactose, dextrose, ethanol, glycerol, albumin, and the like. These compositions may optionally include stabilizers, antioxidants, antimicrobials, preservatives, buffering agents, surfactants, and other accessory additives. A presently preferred vehicle comprises about 1 mg/mL serum albumin in phosphate-buffered saline (PBS). A thorough discussion of suitable vehicles for parenteral administration may be found in E. W. Martin, "Remington's Pharmaceutical Sciences" (Mack Pub. Co., current edition).

The precise dosage necessary will vary with the age, size, and condition of the subject, the nature and severity of the disorder to be treated, and the like: thus, a precise effective amount cannot be specified in advance. However, appropriate amounts may be determined by routine experimentation with animal models. In general terms, an effective dose sFGF-R will range from about 10 μg/Kg to about 5 mg/Kg.

C. Examples

The examples presented below are provided as a further guide to the practitioner of ordinary skill in the art, and are not to be construed as limiting the invention in any way.

Example 1

Procedures

Materials.

Human basic FGF was produced in yeast, as described by P. J. Barr et al, *J Biol Chem* (1988) 263:16471–16478. Enzymes for molecular biology were obtained from Boehringer Mannheim, New England Biolabs and Pharmacia. The λZAP cDNA cloning kit was obtained from Stratagene. The PCR amplification kit was from Perkin Elmer Cetus. Radiochemicals were obtained from Amersham or New England Nuclear. Lentil lectin Sepharose® 4B and methyl-α-D-mannopyranoside were obtained from Sigma. Human liver poly (A)+ RNA was obtained from Clontech (Palo Alto, Calif.) and human osteosarcoma tissue was a gift from Dr. Marshall Urist (University of California, Los Angeles).

Hep G2 (ATCC No. HB 8065), a human hepatoma cell line; 293, a human embryonic kidney cell line (ATCC No. CRL 1573); and *Spodoptera frugiperda* clone 9 (Sf9) an insect cell line, were obtained from the American Type Culture Collection (Rockville, MD). Hep G2 and 293 cells were grown to subconfluency in Dulbecco's modified Eagle's medium (DMEM) containing 10% fetal calf serum, 100 U/mL penicillin and 100 mg/mL streptomycin at 37° C. in 5% $CO_2$. Sf9 cells were adapted to grow in Excell-400 serum free medium (J. R. Scientific). Procedures for culturing and subculturing the cells, transfections and production of high titer viral stocks were performed as described (M. D. Summers & G. E. Smith, (1987) A Manual of Methods of Baculovirus Vectors and Insect Cell Culture Procedures, Texas Agriculture Experiment Station Bulletin No. 1555). Wild type *Autographa californica* nuclear polyhedrosis virus (AcMNPV) viral DNA and transfer plasmid pAc373 were a gift of Dr. Max Summers (Texas A&M University).

Example 2

Expression of EC-FGF Receptor

Oligonucleotide Synthesis

Oligonucleotide adapters, probes and sequencing primers were synthesized by the phosphoramidite method using Applied Biosystems (Foster City, Calif.) model 380A and 380B synthesizers, purified by polyacrylamide gel electrophoresis and desalted on SEP-PAK $C_{18}$ cartridges (Waters, Milford, Mass.). The oligonucleotide probes used for screening the cDNA library were complementary to nucleotides 1–30 (5'-A-TAACGGACCTTGTAGCCTCCAATTCTGTG-3') and nucleotides 1840–1869 (5'-GCGGCGTTTGAGTCCGCCATTGGCAAGCTG-3') of the published flg nucleic acid sequence (M. Ruta et al, supra). The two PCR primers used to amplify the extracellular region of the FGF receptor (flg5) cDNA consisted of a sense primer, P4 (5'-CCAACCT-CTAGAGGATCCACTGGGATGTGGAGCT-GGAAGTGC-3') containing the ribosome binding site plus amino acids 1–6 of FIG. 5 and an antisense primer, P3 (5'-GTAAGCGGCCGCGGATCCTTACTACT-CCAGGTACAGGGGCGA-3') containing amino acids 369–374 of flg5 and directly followed by a termination codon. Both primers contain BamHI sites to facilitate cloning into pAc373. Two additional PCR primers were used to identify two and three immunoglobulinlike domain FGF receptors in various tissues. They were a sense primer, P1 (5'-CCATTT-GGATCCGTCACAGCCACACTCTGCACCGCT-3') encoding amino acids 14 to 21 of FIG. 5 and an antisense primer P2 (5'-CCATTTGTCGACTT-CCATCTTTTCTGGGGATGTCCA-3') encoding the complement of amino acids 154 to 161 of FIG. 5. The primers contain BamHI and SalI sites to facilitate cloning into M13 sequencing plasmids.

RNA Isolation and Construction and Screening of the cDNA Library

RNA was isolated by the guanidinium thiocyanate method (J. M. Chirgwin et al, *Biochem* (1979) 18:5294–5299) with modifications (G. J. Freeman et al, *Proc Natl Acad Sci USA* (1983) 80:4094–4098). Poly(A)+ RNA was purified by a single fractionation over oligo(dT) cellulose (H. Aviv & P. Leder, *Proc Natl Acad Sci USA* (1972) 69:1408–1412). The construction and screening of the Hep G2 library in λZAP has been described (J. Zapf et al, *J Biol Chem* (1990) 265:14892–14898). The probes were labeled with T4 polynucleotide kinase and [γ-$^{32}$P]-ATP (J. Sambrook et al, (1989) Molecular Cloning: A Laboratory Manual (Cold Spring Harbor Laboratory, Cold Spring Harbor, N.Y.), 2nd Ed) to a specific activity of $1-2\times10^8$ cpm/mg. Approximately 600,000 recombinant phages from the Hep G2 cDNA library were screened on duplicate nitrocellulose filters (Millipore, HATF 137), with two flg oligonucleotide probes. Areas of plaques that hybridized to both probes were further purified.

Plasmid Isolation, Subcloning and Sequencing

Bluescript SK(-) plasmids containing the putative flg cDNA inserts were released from λZAP by the M13 rescue/excision protocol described by the supplier (Stratagene). Plasmid DNA was isolated by the alkaline lysis method (J. Sambrook et al, supra). The cDNA inserts containing the putative flg sequence were excised from the Bluescript SK(−) vector by BglII or EcoRI digestion and fractionated by agarose gel electrophoresis. Inserts were excised from the gel and passively eluted for 16 h with gentle shaking in 10 mM Tris-hydrochloride, pH 7.5, 1 mM EDTA (TE), purified on elutip-D columns (Schleicher and Schuell) and subcloned into M13 sequencing vectors (C. Yanisch-Perron et al, *Gene* (1985) 33:103–119). PCR-amplified DNA was similarly purified. DNA sequencing was performed by the dideoxy chain termination method (F. Sanger et al, *Proc Natl Acad Sci USA* (1977) 74:5463–5467) using M13 primers as well as specific internal primers. Ambiguous regions were resolved using 7-deaza-2'-deoxyguanosine-5'-triphosphate (P. J. Barr et al, Biotechniques (1986) 4:428–432) and Sequenase (US Biochemicals).

To isolate full length FGF receptor encoded cDNAs, 600,000 recombinants from a λZAP-human hepatoma cell line (Hep G2) cDNA library were screened with oligonucleotide probes derived from the 5'- and 3'-ends of a partial flg cDNA (M. Ruta et al, supra). Six clones were identified that hybridized to both probes. BglII restriction endonuclease digestion of the cDNA inserts and gel analysis suggested that three of the six clones contained the complete coding sequence. Four BglII fragments of 1.6, 1.1, 0.6, and 0.55 Kb and two EcoRI fragments of 2.7 and 1.2 Kb were identified in the longest cDNA clone, FIG. 5 (FIG. I). BglII and EcoRI sites are also present in the flanking adapters that were used to make the cDNA library. The BglII and EcoRI fragments of FIG. 5 cDNA were isolated, cloned into M13 mp19 and sequenced. A detailed sequencing strategy is shown in FIG. 1. The FIG. 5 cDNA encodes a protein of 820 amino acids and is flanked by 671 and 753 nucleotides of 5'- and 3'-untranslated regions, respectively. The encoded protein revealed a structure that included a signal peptide, three extracellular immunoglobulinlike domains, an acidic amino acid-rich region, a transmembrane domain and a split intracellular tyrosine kinase domain. These domains have been identified previously on the chicken (P. L. Lee et al, supra), the mouse (H. H. Reid et al, supra) and most recently, several human FGF receptors deduced from cDNA sequences (A. Isacchi et al, supra; D. E. Johnson et al, supra). The encoded receptor also contains eight consensus N-linked glycosylation sites in the extracellular region and one in the cytoplasmic tyrosine kinase domain.

The amino acid sequence encoded by FIG. 5 cDNA is shown in FIG. 2 (top row). For comparison, five other previously identified forms of the human FGF receptors are shown (A. Isacchi et al, supra; D. E. Johnson et al, supra) and are aligned for maximum amino acid sequence identity. The identified structural domains are indicated above the FIG. 5 sequence, as are regions corresponding to the PCR primers. The putative signal peptidase cleavage site (G. von Heijne, Nuc Acids Res (1986) 14:4683–4690) after $Ala_{21}$ is indicated ($\downarrow$). Differences or deletions of amino acids are boxed. The three most notable differences between the six FGF receptors are: i) a large deletion near the N-terminus in FGF receptors 3–6 ($aa_{31-119}$) that spans the entire first immunoglobulinlike domain; ii) truncation of receptors 5 and 6, which differ from the other FGF receptors in their carboxyl terminal amino acids ($aa_{221-300}$ and $aa_{223-302}$ respectively), with consequent deletion of their transmembrane and cytoplasmic domains; and iii) deletion of amino acids 148 and 149 in FGF receptors 1, 3 and 5. Other differences in FGF receptor-3 ($aa_{101}$) and FGF receptor-2 also noted. The partial flg sequence M. Ruta et al, Oncogene (1988) 3:9–15) is not shown, but has an N-terminal amino acid corresponding to position 198 of FGF receptor-1. Accordingly, it may be encoded by the cDNAs of FGF receptors 1, 2, 3 or 4. It is important to note however, that the flg sequence displays a difference from FGF receptors 1–4 in the tyrosine kinase domain at $aa_{670-674}$, due to three nucleic acid deletions flanking this region that results in a limited frame shift.

PCR Amplification:

Amplification reactions were performed according to the supplier of the PCR kit (Perkin Elmer Cetus). PCR primers and template were at a final concentration of 1 mM and 0.1–0.5 mg/mL, respectively. The cDNA encoding flg5 was used as a template DNA for the construction of EC-FGF receptor in pAc373. For expression studies, template DNA was reverse transcribed from mRNA as described (J. Zapf et al, supra). 30 cycles of PCR were performed using a Perkin Elmer Cetus DNA thermal cycler. Each cycle consisted of a 94° C., 1 min denaturation step; a 55° C., 2 min annealing step; and a 72° C., 3 min extension step. The extension step in the last cycle was 7 min.

Construction of Recombinant EC-FGF Receptor Virus

The PCR amplified DNA fragment encoding the extracellular domain of the FGF receptor was digested with BamHI, gel purified and ligated to BamHI cut, calf intestinal phosphatase-treated pAc373. Recombinant plasmids were analyzed for EC-FGF receptor cDNAs inserted in the correct orientation by restriction endonuclease digestion and agarose gel electrophoresis.

The recombinant plasmid was cotransfected with wild-type AcMNPV viral DNA into Sf9 cells by the calcium phosphate transfection procedure (M. D. Summers & G. E. Smith, supra). Recombinant viruses were identified in the first round of plaque screening by hybridization with FIG. 5 cDNA that was $^{32}$P-labeled by replacement synthesis (J. Sambrook et al, supra). The recombinant viruses were further purified by visual screening for the occlusion negative phenotype in two additional rounds.

The recombinant baculovirus that expressed EC-FGF receptor was constructed by ligating PCR-amplified DNA encoding amino acids 1–374 of the FIG. 5 cDNA into the BamHI site of the baculovirus transfer vector pAc373. The PCR primers contained flanking BamHI sites to facilitate cloning. In addition, the sense primer (P4) contained, directly upstream from the initiation codon, the −1 to −5 nucleotides of the FIG. 5 cDNA sequence that are implicated in ribosome binding (M. Kozak, Nuc Acids Res (1984) 12:857–87239). The 3'-antisense primer (P3) contained two termination codons TAG and TAA directly after amino acid 374. Co-transfection of Sf9 cells with AcMNPV viral DNA and the recombinant construct (pAc373-EC-FGF receptor) by the calcium phosphate method (M. D. Summers & G. E. Smith, supra) generated recombinant baculovirus that were subsequently purified by plaque hybridization and visual screening.

Expression and Purification of EC-FGF Receptor

Sf9 cells were seeded in T-150 flasks at $5 \times 10^7$ cells/flask for small scale production of EC-FGF receptor. After 2 hr, the cells were infected with recombinant virus and incubated for 68–72 hrs. For larger scale production of EC-FGF receptor, Sf9 cells were infected with recombinant virus, incubated for 1 hr at 25° C., and then incubated in 3L spinner flasks at $3 \times 10^6$ cells/ml for 72–97 hrs. The conditioned medium from the above cultures were centrifuged for 30 min. at 14,000 xg at 4° C. to partially clarify the recombinant virus. An aliquot of the supernatant was analyzed for EC-FGF receptor by 15% trichloroacetic acid precipitation, denaturing SDS-polyacrylamide gel electrophoresis (PAGE) (U.

K. Laemmli, Nature (1970) 227:680-685) and visualization by Coomassie blue staining.

To further purify the EC-FGF receptor, the clarified supernatant was adjusted to 25 mM Hepes, pH 7.3, and loaded onto a lentil lectin Sepharose® 4B column equilibrated with 150 mM NaCl, 25 mM Hepes, pH 7.3, 1 mM CaCl$_2$ and 1 mM MnCl$_2$. The column was washed in this equilibration buffer until no protein could be detected (OD$_{280}$) in the flow-through. The EC-FGF receptor was then eluted with 10% methyl-α-D-mannopyranoside, 25 mM Hepes, pH 7.3. Peak fractions were pooled, concentrated (Centricon 30) and stored in 10 mM Tris, pH 7.0, at −80° C. Aliquots from the various stages of purification were analyzed by SDS-PAGE (U. K. Laemmli, supra) and visualized by Coomassie blue staining.

To analyze EC-FGF receptor expression by the recombinant EC-FGF receptor-containing baculoviruses, Sf9 cells were infected with either wild type AcMNPV or EC-FGF receptor-AcMNPV. After 68 hours of incubation, proteins in the supernatant were precipitated and analyzed by SDS-PAGE and Coomassie blue staining. The resulting gel showed that the most intensely stained protein band in the supernatant ($M_r$=58,000) is present only in the EC-FGF receptor-AoMNPV-infected cells and is not in the AcMNPV-infected cells, suggesting that this protein is the EC-FGF receptor. Six recombinant EC-FGF receptor-containing baculoviruses were analyzed for EC-FGF receptor expression in Sf9 cells. The level of EC-FGF receptor expression was essentially identical.

Analysis of EC-FGF Receptor Oligosaccharides

Oligosaccharides contained in the purified EC-FGF receptor were analyzed by endoglycolytic cleavage with N-glycanase (Genzyme, Boston) according to the supplier's specifications. The products were analyzed by SDS-PAGE (U. K. Laemmli, supra) and visualized by Coomassie blue staining. The expected $M_r$ for an unmodified EC-FGF receptor is ~40,000, suggesting that post-translational modification of the receptor occurs in insect cells. There are eight potential N-glycosylation glycosylation sites in the extracellular region of the FGF receptor to which oligosaccharides may be attached. To determine if N-linked oligosaccharides were present and contributed to the apparent $M_r$ of the EC-FGF, the molecule was digested with N-glycanase. Digestion of EC-FGF receptor reduced the apparent $M_r$ from 58,000 to 52,000, indicating that oligosaccharides were attached to the receptor through asparagine residues. In further support of this result, the EC-FGF receptor was purified by lentil lectin affinity chromatography.

Example 3

FGF Receptor Binding and Activity Assays

Radioreceptor assay

The effects of the EC-FGF receptor on the binding of radioiodinated basic FGF to its receptor was examined using a radioreceptor assay as described in the art. Briefly, baby hamster kidney cells were maintained in Hepes (25 mM) buffered DMEM supplemented with 5% calf serum and antibiotics and were grown to subconfluence in 24-well dishes. The cells were washed twice with phosphate buffered saline and incubated for 3 hours at 4° C. with the indicated concentrations of the peptides and 1 ng (100,000 cpm) of labelled basic FGF in 300 µL of DMEM containing 0.1% gelatin. The medium was aspirated and the cells washed twice with 0.5 mL PBS and twice with 0.5 mL of PBS containing 2 M NaCl. The amount of $^{125}$I-FGF bound to the high affinity receptor was determined by quantitating the amount of radioactivity in the cell lysate obtained with 0.1% Triton® X-100 in PBS, pH 8.4.

Mitogenesis assay

The effects of the peptides on mitogenesis was determined using Swiss 3T3 fibroblasts as described. Briefly, cells were plated at a concentration of 20,000 cells/well in 96 microwells and grown for two days in Hepes (25 mM) buffered DMEM containing 10% fetal calf serum and antibiotics. On the third day, the cells were washed twice with DMEM with no additives and the cells synchronized by a further incubation for two days in 0.5% fetal calf serum. At the time of assay, the test substances (basic FGF, EC-FGFR or both together) were added directly to the cells in 10 µL of DMEM supplemented with 0.1% BSA. Eighteen hours later, 1 µCi of 3H-thymidine was added to the cells, and 24 hours after the addition of the peptides, the media was aspirated, the cells washed with PBS and the proteins precipitated with 50% trichloroacetic acid. After three washes, the cells were solubilized overnight with 1 N NaOH and the amount of radioactivity incorporated into DNA was determined by scintillation counting.

Cell Proliferation Assays

The EC-FGF receptor was tested for its ability to inhibit basic FGF stimulated adrenal capillary endothelial (ACE) cell proliferation. Aliquots of receptor preparation were added to ACE cells and four days later, the cell number was established using a Coulter particle counter. For comparison purposes, 2 ng/ml of recombinant human basic FGF increased cell proliferation from 27,500±2,100 cells/well to 133,300±1,800 cells/well.

Receptor dependent tyrosine phosphorylation

Swiss 3T3 cells were treated at 37° C. for 5 minutes with no additives or with basic FGF (15 ng/mL), EC-FGF receptor (10 mg/mL) or basic FGF (15 ng/mL) and EC-FGF (10 mg/mL) added together. The cells were then harvested in a 2.5× Laemmli's buffer, the proteins separated on 8% polyacrylamide SDS-PAGE gels and the presence of tyrosine phosphorylated proteins examined by Western blotting with a specific anti-phosphotyrosine antibody.

The FGF binding properties of EC-FGF receptor was determined using a soluble binding assay (adapted from the assay described by J. E. Robinson et al, J Immunol Meth (1990) 132:63–71). EC-FGF receptor, attached to concanavalin A coated plastic wells, was incubated with $^{125}$I-bFGF and increasing concentrations of bFGF. Scatchard analysis of $^{125}$I-FGF binding indicated a Kd of less than 5nM. An completely accurate Kd determination was not possible due to the non-specific binding of $^{125}$I-FGF. Several blocking agents included in the assays, such as BSA, gelatin and heparan sulfate, were ineffective at blocking the non-specific binding of 125I-FGF at low concentrations of $^{125}$I-FGF.

The biological activity of the EC-FGF receptor was tested in several additional assay systems. First, the addition of EC-FGF receptor to endothelial cells in culture was shown to inhibit the proliferative effect of basic FGF. Because this cell type is known to synthesize basic FGF, it was suspected that the recombinant receptor might inhibit basal endothelial cell growth. As predicted, the expressed EC-FGF receptor can inhibit basal cell proliferation. Specificity of this effect was studied by incubating various cell types, that do not synthesize basic FGF, with the EC-FGF receptor. No effects were observed on BHK cells, A431 cells or on CHO cells. As expected, however, the addition of EC-FGF receptor to 3T3 cells inhibited the mitogenic response to basic FGF. Furthermore, it was observed that the EC-FGF receptor inhibited the growth of melanoma cells, a cell type previously shown to be dependent on the autocrine production of basic FGF.

To establish that the FGF/EC-FGF receptor complex did not recognize the basic FGF receptor, two experiments were performed. First, the addition of the EC-FGF receptor preparation to BHK cells during the radioreceptor assay prevented the binding of $^{125}$I-basic FGF to its receptor indicating that it binds basic FGF. The binding of $^{125}$I-basic FGF to its low affinity receptor was also inhibited. Secondly, basic FGF fails to activate the tyrosine phosphorylation of either its cell membrane receptor or the characteristic 90-kDa substrate identified by Coughlin et al, *J Biol Chem* (1988) 263:988–993 when incubated in the presence of EC-FGF receptor.

Example 4

Alternate Receptor Forms

To determine whether multiple forms of the FGF receptor mRNAs are expressed in a single tissue or cell type, PCR was performed using mRNA isolated from human liver and osteosarcoma tissue as well as from the hepatoma cell line Hep G2 and the embryonic kidney cell line, 293. For these experiments, we used primers derived from the nucleic acid sequence encoding amino acids 14 to 21 and 154 to 160 of the FIG. 5 cDNA (P1 and P2, FIG. 2). These primers can detect either the two or three immunoglobulinlike-domain transcripts and should yield a 184 bp or 441 bp PCR-generated DNA product, respectively. Additionally, deletion variants at amino acid positions 148 and 149 can be readily identified by DNA sequence analysis of the PCR products. The truncated FGF receptors 5 and 6 shown (FIG. 2), are not distinguished by the primers selected.

Acrylamide gel analysis of the PCR products revealed DNA fragments of the expected size in all four tissues. DNA sequence analysis of the fragments revealed sequences that were identical, between the PCR primers, to the four forms of the FGF receptor shown in FIG. 2 (FGF receptor 1–4). Several additional DNA fragments of approximately 280 bp and 550 bp were observed in all four PCR reactions. These PCR products were sequenced and shown to encode sequences unrelated to the FGF receptor. Thus, at least four forms of the FGF receptor are expressed in the tissues and cell lines examined. Taken together with the previous findings, these results indicate that multiple forms of FGF receptor mRNA are expressed in a wide variety of cell types and that as many as four forms of the receptor may be present on the surface of a cell type. Whether these forms are coexpressed in single cells remains to be determined.

Sequencing of the PCR fragments, identified an additional form of FGF receptor RNA that contained an intervening sequence. This form of the FGF receptor RNA most likely represents incompletely spliced heteronuclear RNA since a splicing event has already deleted the immunoglobulinlike 1 domain (aa$_{31-119}$) Interruption of the encoded amino acid sequence occurred at Pro$_{150}$ (vertical lines A and C) and was separated by 248 nucleotides. This intervening region contains the dinucleotides GT and AG at its 5' and 3' ends, respectively, and is most likely derived from an intron.

The presence of an intron at aa$_{150}$ suggested that an alternate splice donor site 2 amino acids upstream from 150 could generate the variant forms of the FGF receptor lacking amino acids 148 and 149. Indeed, six bases upstream (vertical line B) from amino acid 150, there is an acceptable splice donor site that could substitute for the downstream site and that would generate an in-frame deletion of amino acids 148 and 149. Thus, both the two and three immunoglobulinlike forms of the FGF receptor as well as the variant forms at amino acids 148 and 149 can be explained by alternate splicing.

---

We claim:

1. An essentially pure human fibroblast growth factor receptor comprising an amino acid sequence as shown in FIG. 2, sequence 1 (Sequence ID #1).

2. The receptor of claim 1, wherein the receptor is a recombinant human fibroblast growth factor receptor.

3. A fragment of a human fibroblast growth factor receptor comprising an amino acid sequence shown as amino acid residues 1-374 of FIG. 2, sequence 1 (Sequence ID#1).

* * * * *

UNITED STATES PATENT AND TRADEMARK OFFICE
CERTIFICATE OF CORRECTION

PATENT NO.   : 5,229,501
DATED        : July 20, 1993
INVENTOR(S)  : Michael C. Keifer, Pablo D. T. Valenzuela, and Philip J. Barr It is certified that error appears in the above-identified patent and that said Letters Patent is hereby corrected as shown below:

Columns 15-16, SEQ ID NO: 1,
Line 6, delete amino acids 138-140.
Line 16, delete amino acid 296 (Trp) and substitute therefor "Val Asn".
Line 18, delete amino acid 324 (Phe) and substitute therefor "Glu".
Line 21, after amino acid 370 (Thr) insert "Ser Pro Leu Tyr Leu".

Columns 17-18, SEQ ID NO: 1,
Line 10, after amino acid 629 (Asp) insert "Asn".
Line 18, delete amino acid 759 (Ala) and substitute therefor "Glu".

Signed and Sealed this

Eighteenth Day of December, 2001

Attest:

JAMES E. ROGAN
*Attesting Officer*   *Director of the United States Patent and Trademark Office*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 816 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Met  Trp  Ser  Trp  Lys  Cys  Leu  Leu  Phe  Trp  Ala  Val  Leu  Val  Thr  Ala
 1                   5                        10                       15

Thr  Leu  Cys  Thr  Ala  Arg  Pro  Ser  Pro  Thr  Leu  Pro  Glu  Gln  Ala  Gln
               20                       25                       30

Pro  Trp  Gly  Ala  Pro  Val  Glu  Val  Glu  Ser  Phe  Leu  Val  His  Pro  Gly
               35                       40                       45
```

```
Asp  Leu  Leu  Gln  Leu  Arg  Cys  Arg  Leu  Arg  Asp  Asp  Val  Gln  Ser  Ile
 50                  55                       60
Asn  Trp  Leu  Arg  Asp  Gly  Val  Gln  Leu  Ala  Glu  Ser  Asn  Arg  Thr  Arg
 65                       70                  75                            80
Ile  Thr  Gly  Glu  Glu  Val  Glu  Val  Gln  Asp  Ser  Val  Pro  Ala  Asp  Ser
                         85                  90                       95
Gly  Leu  Tyr  Ala  Cys  Val  Thr  Ser  Ser  Pro  Ser  Gly  Ser  Asp  Thr  Thr
               100                 105                      110
Tyr  Phe  Ser  Val  Asn  Val  Ser  Asp  Ala  Leu  Pro  Ser  Ser  Glu  Asp  Asp
          115                      120                      125
Asp  Asp  Asp  Asp  Asp  Ser  Ser  Ser  Glu  Glu  Lys  Lys  Glu  Lys  Glu  Thr
130                      135                 140
Asp  Asn  Thr  Lys  Pro  Asn  Pro  Val  Ala  Pro  Tyr  Trp  Thr  Ser  Pro  Glu
145                      150                 155                           160
Lys  Met  Glu  Lys  Lys  Leu  His  Ala  Val  Pro  Ala  Ala  Lys  Thr  Val  Lys
                    165                      170                      175
Phe  Lys  Cys  Pro  Ser  Ser  Gly  Thr  Pro  Asn  Pro  Thr  Leu  Arg  Trp  Leu
               180                      185                      190
Lys  Asn  Gly  Lys  Glu  Phe  Lys  Pro  Asp  His  Arg  Ile  Gly  Gly  Tyr  Lys
          195                      200                      205
Val  Arg  Tyr  Ala  Thr  Trp  Ser  Ile  Ile  Met  Asp  Ser  Val  Val  Pro  Ser
210                      215                      220
Asp  Lys  Gly  Asn  Tyr  Thr  Cys  Ile  Val  Glu  Asn  Glu  Tyr  Gly  Ser  Ile
225                      230                      235                      240
Asn  His  Thr  Tyr  Gln  Leu  Asp  Val  Val  Glu  Arg  Ser  Pro  His  Arg  Pro
                    245                      250                      255
Ile  Leu  Gln  Ala  Gly  Leu  Pro  Ala  Asn  Lys  Thr  Val  Ala  Leu  Gly  Ser
               260                      265                      270
Asn  Val  Glu  Phe  Met  Cys  Lys  Val  Tyr  Ser  Asp  Pro  Gln  Pro  His  Ile
          275                      280                      285
Gln  Trp  Leu  Lys  His  Ile  Glu  Trp  Gly  Ser  Lys  Ile  Gly  Pro  Asp  Asn
290                      295                      300
Leu  Pro  Tyr  Val  Gln  Ile  Leu  Lys  Thr  Ala  Gly  Val  Asn  Thr  Thr  Asp
305                      310                      315                      320
Lys  Glu  Met  Phe  Val  Leu  His  Leu  Arg  Asn  Val  Ser  Phe  Glu  Asp  Ala
                    325                      330                      335
Gly  Glu  Tyr  Thr  Cys  Leu  Ala  Gly  Asn  Ser  Ile  Gly  Leu  Ser  His  His
               340                      345                      350
Ser  Ala  Trp  Leu  Thr  Val  Leu  Glu  Ala  Leu  Glu  Glu  Arg  Pro  Ala  Val
          355                      360                      365
Met  Thr  Glu  Ile  Ile  Ile  Tyr  Cys  Thr  Gly  Ala  Phe  Leu  Ile  Ser  Cys
370                      375                      380
Met  Val  Gly  Ser  Val  Ile  Val  Tyr  Lys  Met  Lys  Ser  Gly  Thr  Lys  Lys
385                      390                      395                      400
Ser  Asp  Phe  His  Ser  Gln  Met  Ala  Val  His  Lys  Leu  Ala  Lys  Ser  Ile
                    405                      410                      415
Pro  Leu  Arg  Arg  Gln  Val  Thr  Val  Ser  Ala  Asp  Ser  Ser  Ala  Ser  Met
               420                      425                      430
Asn  Ser  Gly  Val  Leu  Leu  Val  Arg  Pro  Ser  Arg  Leu  Ser  Ser  Ser  Gly
          435                      440                      445
Thr  Pro  Met  Leu  Ala  Gly  Val  Ser  Glu  Tyr  Glu  Leu  Pro  Glu  Asp  Pro
          450                      455                      460
Arg  Trp  Glu  Leu  Pro  Arg  Asp  Arg  Leu  Val  Leu  Gly  Lys  Pro  Leu  Gly
465                      470                      475                      480
```

| | | | | | | | | | | | | | | |
|---|---|---|---|---|---|---|---|---|---|---|---|---|---|---|
|Glu|Gly|Cys|Phe|Gly|Gln|Val|Val|Leu|Ala|Glu|Ala|Ile|Gly|Leu|Asp|
| | | | |485| | | |490| | | | |495| |
|Lys|Asp|Lys|Pro|Asn|Arg|Val|Thr|Lys|Val|Ala|Val|Lys|Met|Leu|Lys|
| | | |500| | | |505| | | |510| | | |
|Ser|Asp|Ala|Thr|Glu|Lys|Asp|Leu|Ser|Asp|Leu|Ile|Ser|Glu|Met|Glu|
| | |515| | | |520| | | |525| | | | |
|Met|Met|Lys|Met|Ile|Gly|Lys|His|Lys|Asn|Ile|Ile|Asn|Leu|Leu|Gly|
|530| | | | |535| | | | |540| | | | | |
|Ala|Cys|Thr|Gln|Asp|Gly|Pro|Leu|Tyr|Val|Ile|Val|Glu|Tyr|Ala|Ser|
|545| | | |550| | | |555| | | | |560| | |
|Lys|Gly|Asn|Leu|Arg|Glu|Tyr|Leu|Gln|Ala|Arg|Arg|Pro|Pro|Gly|Leu|
| | | |565| | | |570| | | | |575| | | |
|Glu|Tyr|Cys|Tyr|Asn|Pro|Ser|His|Asn|Pro|Glu|Glu|Gln|Leu|Ser|Ser|
| | |580| | | |585| | | | |590| | | | |
|Lys|Asp|Leu|Val|Ser|Cys|Ala|Tyr|Gln|Val|Ala|Arg|Gly|Met|Glu|Tyr|
| |595| | | |600| | | |605| | | | | | |
|Leu|Ala|Ser|Lys|Lys|Cys|Ile|His|Arg|Asp|Leu|Ala|Ala|Arg|Asn|Val|
|610| | | |615| | | |620| | | | | | | |
|Leu|Val|Thr|Glu|Asp|Val|Met|Lys|Ile|Ala|Asp|Phe|Gly|Leu|Ala|Arg|
|625| |630| | | | |635| | | | |640| | | |
|Asp|Ile|His|His|Ile|Asp|Tyr|Tyr|Lys|Lys|Thr|Thr|Asn|Gly|Arg|Leu|
| | | |645| | | | |650| | | | |655| | |
|Pro|Val|Lys|Trp|Met|Ala|Pro|Glu|Ala|Leu|Phe|Asp|Arg|Ile|Tyr|Thr|
| | |660| | | |665| | | | |670| | | | |
|His|Gln|Ser|Asp|Val|Trp|Ser|Phe|Gly|Val|Leu|Leu|Trp|Glu|Ile|Phe|
| | |675| | | |680| | | | |685| | | | |
|Thr|Leu|Gly|Gly|Ser|Pro|Tyr|Pro|Gly|Val|Pro|Val|Glu|Glu|Leu|Phe|
| |690| | | | |695| | | |700| | | | | |
|Lys|Leu|Leu|Lys|Glu|Gly|His|Arg|Met|Asp|Lys|Pro|Ser|Asn|Cys|Thr|
|705| | | |710| | | |715| | | | | |720| |
|Asn|Glu|Leu|Tyr|Met|Met|Met|Arg|Asp|Cys|Trp|His|Ala|Val|Pro|Ser|
| | | |725| | | |730| | | | |735| | | |
|Gln|Arg|Pro|Thr|Phe|Lys|Gln|Leu|Val|Glu|Asp|Leu|Asp|Arg|Ile|Val|
| | |740| | | |745| | | | |750| | | | |
|Ala|Leu|Thr|Ser|Asn|Gln|Ala|Tyr|Leu|Asp|Leu|Ser|Met|Pro|Leu|Asp|
| |755| | | | |760| | | | |765| | | | |
|Gln|Tyr|Ser|Pro|Ser|Phe|Pro|Asp|Thr|Arg|Ser|Ser|Thr|Cys|Ser|Ser|
|770| | | | |775| | | | |780| | | | | |
|Gly|Glu|Asp|Ser|Val|Phe|Ser|His|Glu|Pro|Leu|Pro|Glu|Glu|Pro|Cys|
|785| | | |790| | | |795| | | | | | |800|
|Leu|Pro|Arg|His|Pro|Ala|Gln|Leu|Ala|Asn|Gly|Gly|Leu|Lys|Arg|Arg|
| | | |805| | | |810| | | | |815| | | |

( 2 ) INFORMATION FOR SEQ ID NO:2:

( i ) SEQUENCE CHARACTERISTICS:
( A ) LENGTH: 817 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

| | | | | | | | | | | | | | | |
|---|---|---|---|---|---|---|---|---|---|---|---|---|---|---|
|Met|Trp|Ser|Trp|Lys|Cys|Leu|Leu|Phe|Trp|Ala|Val|Leu|Val|Thr|Ala|
|1| | | |5| | | | |10| | | | |15| |
|Thr|Leu|Cys|Thr|Ala|Arg|Pro|Ser|Pro|Thr|Leu|Pro|Glu|Gln|Ala|Gln|
| | |20| | | | |25| | | | |30| | | |

```
Pro  Trp  Gly  Ala  Pro  Val  Glu  Val  Glu  Ser  Phe  Leu  Val  His  Pro  Gly
          35                  40                       45
Asp  Leu  Leu  Gln  Leu  Arg  Cys  Arg  Leu  Arg  Asp  Asp  Val  Gln  Ser  Ile
     50                  55                  60
Asn  Trp  Leu  Arg  Asp  Gly  Val  Gln  Leu  Ala  Glu  Ser  Asn  Arg  Thr  Arg
65                       70                  75                            80
Ile  Thr  Gly  Glu  Glu  Val  Glu  Val  Gln  Asp  Ser  Val  Pro  Ala  Asp  Ser
                    85                  90                  95
Gly  Leu  Tyr  Ala  Cys  Val  Thr  Ser  Ser  Pro  Ser  Gly  Ser  Asp  Thr  Thr
               100                 105                      110
Tyr  Phe  Ser  Val  Asn  Val  Ser  Asp  Ala  Leu  Pro  Ser  Ser  Glu  Asp  Asp
          115                      120                 125
Asp  Asp  Asp  Asp  Asp  Ser  Ser  Ser  Glu  Glu  Lys  Glu  Thr  Asp  Asn  Thr
     130                      135                 140
Lys  Pro  Asn  Arg  Met  Pro  Val  Ala  Pro  Tyr  Trp  Thr  Ser  Pro  Glu  Lys
145                      150                      155                      160
Met  Glu  Lys  Lys  Leu  His  Ala  Val  Pro  Ala  Ala  Lys  Thr  Val  Lys  Phe
                    165                 170                      175
Lys  Cys  Pro  Ser  Ser  Gly  Thr  Pro  Asn  Pro  Thr  Leu  Arg  Trp  Leu  Lys
               180                 185                      190
Asn  Gly  Lys  Glu  Phe  Lys  Pro  Asp  His  Arg  Ile  Gly  Gly  Tyr  Lys  Val
          195                      200                 205
Arg  Tyr  Ala  Thr  Trp  Ser  Ile  Ile  Met  Asp  Ser  Val  Val  Pro  Ser  Asp
     210                      215                 220
Lys  Gly  Asn  Tyr  Thr  Cys  Ile  Val  Glu  Asn  Glu  Tyr  Gly  Ser  Ile  Asn
225                      230                 235                           240
His  Thr  Tyr  Gln  Leu  Asp  Val  Val  Glu  Arg  Ser  Pro  His  Arg  Pro  Ile
               245                      250                      255
Leu  Gln  Ala  Gly  Leu  Pro  Ala  Asn  Lys  Thr  Val  Ala  Leu  Gly  Ser  Asn
               260                 265                      270
Val  Glu  Phe  Met  Cys  Lys  Val  Tyr  Ser  Asp  Pro  Gln  Pro  His  Ile  Gln
          275                 280                      285
Trp  Leu  Lys  His  Ile  Glu  Val  Asn  Gly  Ser  Lys  Ile  Gly  Pro  Asp  Asn
     290                      295                 300
Leu  Pro  Tyr  Val  Gln  Ile  Leu  Lys  Thr  Ala  Gly  Val  Asn  Thr  Thr  Asp
305                      310                 315                           320
Lys  Glu  Met  Glu  Val  Leu  His  Leu  Arg  Asn  Val  Ser  Phe  Glu  Asp  Ala
               325                      330                 335
Gly  Glu  Tyr  Thr  Cys  Leu  Ala  Gly  Asn  Ser  Ile  Gly  Leu  Ser  His  His
               340                      345                 350
Ser  Ala  Trp  Leu  Thr  Val  Leu  Glu  Ala  Leu  Glu  Glu  Arg  Pro  Ala  Val
          355                      360                 365
Met  Thr  Ser  Pro  Leu  Tyr  Leu  Glu  Ile  Ile  Ile  Tyr  Cys  Thr  Gly  Ala
     370                      375                 380
Phe  Leu  Ile  Ser  Cys  Met  Val  Gly  Ser  Val  Ile  Val  Tyr  Lys  Met  Lys
385                      390                 395                           400
Ser  Gly  Thr  Lys  Lys  Ser  Asp  Phe  His  Ser  Gln  Met  Ala  Val  His  Lys
               405                      410                 415
Leu  Ala  Lys  Ser  Ile  Pro  Leu  Arg  Arg  Gln  Val  Thr  Val  Ser  Ala  Asp
               420                      425                 430
Ser  Ser  Ala  Ser  Met  Asn  Ser  Gly  Val  Leu  Leu  Val  Arg  Pro  Ser  Arg
          435                      440                 445
Leu  Ser  Ser  Ser  Gly  Thr  Pro  Met  Leu  Ala  Gly  Val  Ser  Glu  Tyr  Glu
     450                      455                 460
Leu  Pro  Glu  Asp  Pro  Arg  Trp  Glu  Leu  Pro  Arg  Asp  Arg  Leu  Val  Leu
```

```
                465                     470                     475                     480
        Gly  Lys  Leu  Gly  Glu  Gly  Cys  Phe  Gly  Gln  Val  Val  Glu  Ala  Ile  Gly
                              485                     490                     495

Leu  Asp  Lys  Asp  Lys  Pro  Asn  Arg  Val  Thr  Lys  Val  Ala  Val  Lys  Met
                         500                     505                     510

Leu  Lys  Ser  Asp  Ala  Thr  Glu  Lys  Asp  Leu  Ser  Asp  Leu  Ile  Ser  Glu
                         515                     520                     525

Met  Glu  Met  Met  Lys  Met  Ile  Gly  Lys  His  Lys  Asn  Ile  Ile  Asn  Leu
             530                     535                     540

Leu  Gly  Ala  Cys  Thr  Gln  Asp  Gly  Pro  Leu  Tyr  Val  Ile  Val  Glu  Tyr
        545                     550                     555                     560

Ala  Ser  Lys  Gly  Asn  Leu  Arg  Glu  Tyr  Leu  Gln  Ala  Arg  Arg  Pro  Pro
                              565                     570                     575

Gly  Leu  Glu  Tyr  Cys  Tyr  Asn  Pro  Ser  His  Asn  Pro  Glu  Glu  Gln  Leu
                         580                     585                     590

Ser  Ser  Lys  Asp  Leu  Val  Ser  Cys  Ala  Tyr  Gln  Val  Ala  Arg  Gly  Met
                         595                     600                     605

Glu  Tyr  Leu  Ala  Ser  Lys  Lys  Cys  Ile  His  Arg  Asp  Leu  Ala  Ala  Arg
             610                     615                     620

Asn  Val  Leu  Val  Thr  Glu  Asp  Val  Met  Lys  Ile  Ala  Asp  Phe  Gly  Leu
        625                     630                     635                     640

Ala  Arg  Asp  Ile  His  His  Ile  Asp  Tyr  Tyr  Lys  Lys  Thr  Thr  Asn  Gly
                              645                     650                     655

Arg  Leu  Pro  Val  Lys  Trp  Met  Ala  Pro  Glu  Ala  Leu  Phe  Asp  Arg  Ile
                         660                     665                     670

Tyr  Thr  His  Gln  Ser  Asp  Val  Trp  Ser  Phe  Gly  Val  Leu  Leu  Trp  Glu
                         675                     680                     685

Ile  Phe  Thr  Leu  Gly  Gly  Ser  Pro  Tyr  Pro  Gly  Val  Pro  Val  Glu  Glu
             690                     695                     700

Leu  Phe  Lys  Leu  Leu  Lys  Glu  Gly  His  Arg  Asp  Lys  Pro  Ser  Asn  Cys
        705                     710                     715                     720

Thr  Asn  Glu  Leu  Tyr  Met  Met  Met  Arg  Asp  Cys  Trp  His  Ala  Val  Pro
                              725                     730                     735

Ser  Gln  Arg  Pro  Thr  Phe  Lys  Gln  Leu  Val  Glu  Asp  Leu  Asp  Arg  Ile
                         740                     745                     750

Val  Ala  Leu  Thr  Ser  Asn  Gln  Glu  Tyr  Leu  Asp  Leu  Ser  Met  Pro  Leu
                         755                     760                     765

Asp  Gln  Tyr  Ser  Pro  Ser  Phe  Pro  Asp  Thr  Arg  Ser  Ser  Thr  Cys  Ser
             770                     775                     780

Ser  Gly  Glu  Asp  Ser  Val  Phe  Ser  His  Glu  Pro  Leu  Pro  Glu  Glu  Pro
        785                     790                     795                     800

Cys  Leu  Pro  Arg  His  Pro  Ala  Gln  Leu  Ala  Asn  Arg  Gly  Leu  Lys  Arg
                              805                     810                     815

Arg
```

(2) INFORMATION FOR SEQ ID NO:3:

(i) SEQUENCE CHARACTERISTICS:
    (A) LENGTH: 729 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:3:

```
        Met  Trp  Ser  Trp  Lys  Cys  Leu  Leu  Phe  Trp  Ala  Val  Leu  Val  Thr  Ala
        1                   5                       10                      15
```

-continued

| | | | | | | | | | | | | | | |
|---|---|---|---|---|---|---|---|---|---|---|---|---|---|---|
|Thr|Leu|Cys 20|Thr|Ala|Arg|Pro|Ser|Pro 25|Thr|Leu|Pro|Glu|Gln 30|Asp|Ala|
|Leu|Pro|Ser 35|Ser|Glu|Asp|Asp 40|Asp|Asp|Asp|Asp|Ser 45|Ser|Ser|Glu|
|Glu|Lys 50|Glu|Thr|Asp|Asn|Thr 55|Lys|Pro|Asn|Pro 60|Val|Ala|Pro|Tyr|Trp|
|Thr 65|Ser|Pro|Glu|Lys|Met 70|Glu|Lys|Lys|Leu|His 75|Ala|Val|Pro|Ala|Ala 80|
|Lys|Thr|Val|Lys|Phe 85|Lys|Cys|Pro|Ser|Ser 90|Gly|Thr|Pro|Asn 95|Pro|Thr|
|Leu|Arg|Trp|Ile 100|Gly|Lys|Glu|Phe|Lys 105|Pro|Asp|His|Arg|Ile 110|Gly|Gly|
|Tyr|Lys|Val 115|Arg|Tyr|Ala|Thr|Trp 120|Ser|Ile|Ile|Met|Asp 125|Ser|Val|Val|
|Pro|Ser|Asp 130|Lys|Gly|Asn|Tyr 135|Thr|Cys|Ile|Val|Glu 140|Asn|Glu|Tyr|Gly|
|Ser|Ile 145|Asn|His|Thr|Tyr 150|Gln|Leu|Asp|Val|Val 155|Glu|Arg|Ser|Pro|His 160|
|Arg|Pro|Ile|Leu|Gln 165|Ala|Gly|Leu|Pro|Ala 170|Asn|Lys|Thr|Val|Ala 175|Leu|
|Gly|Ser|Asn|Val 180|Glu|Phe|Met|Cys|Lys 185|Val|Tyr|Ser|Asp|Pro 190|Gln|Pro|
|His|Ile|Gln|Trp 195|Leu|Lys|His|Ile 200|Glu|Val|Asn|Gly|Ser 205|Lys|Ile|Gly|
|Pro|Asp 210|Asn|Leu|Pro|Tyr|Val 215|Gln|Ile|Leu|Lys|Thr 220|Ala|Gly|Val|Asn|
|Thr 225|Thr|Asp|Lys|Glu|Met 230|Glu|Val|Leu|His|Leu 235|Arg|Asn|Val|Ser|Phe 240|
|Glu|Asp|Ala|Gly|Glu 245|Tyr|Thr|Cys|Leu|Ala 250|Gly|Asn|Ser|Ile|Gly 255|Leu|
|Ser|His|His|Ser 260|Ala|Trp|Leu|Thr|Val 265|Leu|Glu|Ala|Leu|Glu 270|Glu|Arg|
|Pro|Ala|Val|Met 275|Thr|Ser|Pro|Leu|Tyr 280|Leu|Glu|Ile|Ile|Ile 285|Tyr|Cys|
|Thr|Gly 290|Ala|Phe|Leu|Ile|Ser 295|Cys|Met|Val|Gly|Ser 300|Val|Ile|Val|Tyr|
|Lys 305|Met|Lys|Ser|Gly|Thr 310|Lys|Lys|Ser|Asp|Phe 315|His|Ser|Gln|Met|Ala 320|
|Val|His|Lys|Leu|Ala 325|Lys|Ser|Ile|Pro|Leu 330|Arg|Arg|Gln|Val|Thr 335|Val|
|Ser|Ala|Asp|Ser 340|Ser|Ala|Ser|Met|Asn 345|Ser|Gly|Val|Leu|Leu 350|Val|Arg|
|Pro|Ser|Arg 355|Leu|Ser|Ser|Ser|Gly 360|Thr|Pro|Met|Leu|Ala 365|Gly|Val|Ser|
|Glu|Tyr 370|Glu|Leu|Pro|Glu|Asp 375|Pro|Arg|Trp|Glu|Leu 380|Pro|Arg|Asp|Arg|
|Leu 385|Val|Leu|Gly|Lys|Pro 390|Leu|Gly|Glu|Gly|Cys 395|Phe|Gly|Gln|Val|Val 400|
|Leu|Ala|Glu|Ala|Ile 405|Gly|Leu|Asp|Lys|Asp 410|Lys|Pro|Asn|Arg|Val 415|Thr|
|Lys|Val|Ala|Val 420|Lys|Met|Leu|Lys|Ser 425|Asp|Ala|Thr|Glu|Lys 430|Asp|Leu|
|Ser|Asp|Leu 435|Ile|Ser|Glu|Met|Glu 440|Met|Met|Lys|Met|Ile 445|Gly|Lys|His|

```
Lys  Asn  Ile  Ile  Asn  Leu  Leu  Gly  Ala  Cys  Thr  Gln  Asp  Gly  Pro  Leu
     450                 455                 460

Tyr  Val  Ile  Val  Glu  Tyr  Ala  Ser  Lys  Gly  Asn  Leu  Arg  Glu  Tyr  Leu
465                      470                 475                           480

Gln  Ala  Arg  Arg  Pro  Pro  Gly  Leu  Glu  Tyr  Cys  Tyr  Asn  Pro  Ser  His
               485                      490                      495

Asn  Pro  Glu  Glu  Gln  Leu  Ser  Ser  Lys  Asp  Leu  Val  Ser  Cys  Ala  Tyr
               500                 505                      510

Gln  Val  Ala  Arg  Gly  Met  Glu  Tyr  Leu  Ala  Ser  Lys  Lys  Cys  Ile  His
          515                 520                      525

Arg  Asp  Leu  Ala  Ala  Arg  Asn  Val  Leu  Val  Thr  Glu  Asp  Asn  Val  Met
     530                 535                 540

Lys  Ile  Ala  Asp  Phe  Gly  Leu  Ala  Arg  Asp  Ile  His  His  Ile  Asp  Tyr
545                 550                 555                           560

Tyr  Lys  Lys  Thr  Thr  Asn  Gly  Arg  Leu  Pro  Val  Lys  Trp  Met  Ala  Pro
               565                      570                      575

Glu  Ala  Leu  Phe  Asp  Arg  Ile  Tyr  Thr  His  Gln  Ser  Asp  Val  Trp  Ser
               580                 585                      590

Phe  Gly  Val  Leu  Leu  Trp  Glu  Ile  Phe  Thr  Leu  Gly  Gly  Ser  Pro  Tyr
          595                 600                      605

Pro  Gly  Val  Pro  Val  Glu  Glu  Leu  Phe  Lys  Leu  Leu  Lys  Glu  Gly  His
     610                 615                      620

Arg  Met  Asp  Lys  Pro  Ser  Asn  Cys  Thr  Asn  Glu  Leu  Tyr  Met  Met  Met
625                      630                 635                           640

Arg  Asp  Cys  Trp  His  Ala  Val  Pro  Ser  Gln  Arg  Pro  Thr  Phe  Lys  Gln
               645                      650                      655

Leu  Val  Glu  Asp  Leu  Asp  Arg  Ile  Val  Ala  Leu  Thr  Ser  Asn  Gln  Glu
               660                 665                      670

Tyr  Leu  Asp  Leu  Ser  Met  Pro  Leu  Asp  Gln  Tyr  Ser  Pro  Ser  Phe  Pro
          675                 680                      685

Asp  Thr  Arg  Ser  Ser  Thr  Cys  Ser  Ser  Gly  Glu  Asp  Ser  Val  Phe  Ser
     690                 695                 700

His  Glu  Pro  Leu  Pro  Glu  Glu  Pro  Cys  Leu  Pro  Arg  His  Pro  Ala  Gln
705                      710                 715                           720

Leu  Ala  Asn  Gly  Gly  Leu  Lys  Arg  Arg
                    725
```

( 2 ) INFORMATION FOR SEQ ID NO:4:

( i ) SEQUENCE CHARACTERISTICS:
        ( A ) LENGTH: 733 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Met  Trp  Ser  Trp  Lys  Cys  Leu  Leu  Phe  Trp  Ala  Val  Leu  Val  Thr  Ala
1                   5                   10                            15

Thr  Leu  Cys  Thr  Ala  Arg  Pro  Ser  Pro  Thr  Leu  Pro  Glu  Gln  Asp  Ala
          20                      25                      30

Leu  Pro  Ser  Ser  Glu  Asp  Asp  Asp  Asp  Asp  Asp  Ser  Ser  Ser  Glu
          35                 40                      45

Glu  Lys  Glu  Thr  Asp  Asn  Thr  Lys  Pro  Asn  Arg  Met  Pro  Val  Ala  Pro
     50                 55                      60

Tyr  Trp  Thr  Ser  Pro  Glu  Lys  Met  Glu  Lys  Lys  Leu  His  Ala  Val  Pro
65                  70                  75                            80
```

```
Ala  Ala  Lys  Thr  Val  Lys  Phe  Lys  Cys  Pro  Ser  Ser  Gly  Thr  Pro  Asn
                    85                  90                      95

Pro  Thr  Leu  Arg  Trp  Leu  Lys  Asn  Gly  Lys  Glu  Phe  Lys  Pro  Asp  His
               100                 105                     110

Arg  Ile  Gly  Gly  Tyr  Lys  Val  Arg  Tyr  Ala  Thr  Trp  Ser  Ile  Ile  Met
          115                      120                     125

Asp  Ser  Val  Val  Pro  Ser  Asp  Lys  Gly  Asn  Tyr  Thr  Cys  Ile  Val  Glu
     130                      135                     140

Asn  Glu  Tyr  Gly  Ser  Ile  Asn  His  Thr  Tyr  Gln  Leu  Asp  Val  Val  Glu
145                      150                      155                          160

Arg  Ser  Pro  His  Arg  Pro  Ile  Leu  Gln  Ala  Gly  Leu  Pro  Ala  Asn  Lys
                    165                      170                          175

Thr  Val  Ala  Leu  Gly  Ser  Asn  Val  Glu  Phe  Met  Cys  Lys  Val  Tyr  Ser
               180                      185                     190

Asp  Pro  Gln  Pro  His  Ile  Gln  Trp  Leu  Lys  His  Ile  Glu  Val  Asn  Gly
               195                      200                     205

Ser  Lys  Ile  Gly  Pro  Asp  Asn  Leu  Pro  Tyr  Val  Gln  Ile  Leu  Lys  Thr
     210                      215                     220

Ala  Gly  Val  Asn  Thr  Thr  Asp  Lys  Glu  Met  Glu  Val  Leu  His  Leu  Arg
225                      230                      235                          240

Asn  Val  Ser  Phe  Glu  Asp  Ala  Gly  Glu  Tyr  Thr  Cys  Leu  Ala  Gly  Asn
                    245                      250                          255

Ser  Ile  Gly  Leu  Ser  His  His  Ser  Ala  Trp  Leu  Thr  Val  Leu  Glu  Ala
               260                      265                     270

Leu  Glu  Glu  Arg  Pro  Ala  Val  Met  Thr  Ser  Pro  Leu  Tyr  Leu  Glu  Ile
          275                      280                     285

Ile  Ile  Tyr  Cys  Thr  Gly  Ala  Phe  Leu  Ile  Ser  Cys  Met  Val  Gly  Ser
     290                      295                     300

Val  Ile  Val  Tyr  Lys  Met  Lys  Ser  Gly  Thr  Lys  Lys  Ser  Asp  Phe  His
305                      310                     315                          320

Ser  Gln  Met  Ala  Val  His  Lys  Leu  Ala  Lys  Ser  Ile  Pro  Leu  Arg  Arg
               325                      330                          335

Gln  Val  Thr  Val  Ser  Ala  Asp  Ser  Ser  Ala  Ser  Met  Asn  Ser  Gly  Val
               340                      345                     350

Leu  Leu  Val  Arg  Pro  Ser  Arg  Leu  Ser  Ser  Ser  Gly  Thr  Pro  Met  Leu
          355                      360                     365

Ala  Gly  Val  Ser  Glu  Tyr  Glu  Leu  Pro  Glu  Asp  Pro  Arg  Trp  Glu  Leu
370                      375                     380

Pro  Arg  Asp  Arg  Leu  Val  Leu  Gly  Lys  Pro  Leu  Gly  Glu  Gly  Cys  Phe
385                      390                     395                          400

Gly  Gln  Val  Val  Leu  Ala  Glu  Ala  Ile  Gly  Leu  Asp  Lys  Asp  Lys  Pro
               405                      410                     415

Asn  Arg  Val  Thr  Lys  Val  Ala  Val  Lys  Met  Leu  Lys  Ser  Asp  Ala  Thr
               420                      425                     430

Glu  Lys  Asp  Leu  Ser  Asp  Leu  Ile  Ser  Glu  Met  Glu  Met  Met  Lys  Met
          435                      440                     445

Ile  Gly  Lys  His  Lys  Asn  Ile  Ile  Asn  Leu  Leu  Gly  Ala  Cys  Thr  Gln
     450                      455                     460

Asp  Gly  Pro  Leu  Tyr  Val  Ile  Val  Glu  Tyr  Ala  Ser  Lys  Gly  Asn  Leu
465                      470                     475                          480

Arg  Glu  Tyr  Leu  Gln  Ala  Arg  Arg  Pro  Pro  Gly  Leu  Glu  Tyr  Cys  Tyr
               485                      490                     495

Asn  Pro  Ser  His  Asn  Pro  Glu  Glu  Gln  Leu  Ser  Ser  Lys  Asp  Leu  Val
               500                      505                     510

Ser  Cys  Ala  Tyr  Gln  Val  Ala  Arg  Gly  Met  Glu  Tyr  Leu  Ala  Ser  Lys
```

-continued

|  |  |  | 515 |  |  |  |  | 520 |  |  |  |  | 525 |  |  |
|---|---|---|---|---|---|---|---|---|---|---|---|---|---|---|---|
| Lys | Cys | Ile | His | Arg | Asp | Leu | Ala | Ala | Arg | Asn | Val | Leu | Val | Thr | Glu |
|  |  | 530 |  |  |  |  | 535 |  |  |  |  | 540 |  |  |  |
| Asp | Asn | Val | Met | Lys | Ile | Ala | Asp | Phe | Gly | Leu | Ala | Arg | Asp | Ile | His |
| 545 |  |  |  |  | 550 |  |  |  |  | 555 |  |  |  |  | 560 |
| His | Ile | Asp | Tyr | Tyr | Lys | Lys | Thr | Thr | Asn | Gly | Arg | Leu | Pro | Val | Lys |
|  |  |  |  | 565 |  |  |  |  | 570 |  |  |  |  | 575 |  |
| Trp | Met | Ala | Pro | Glu | Ala | Leu | Phe | Asp | Arg | Ile | Tyr | Thr | His | Gln | Ser |
|  |  |  | 580 |  |  |  |  | 585 |  |  |  |  | 590 |  |  |
| Asp | Val | Trp | Ser | Phe | Gly | Val | Leu | Leu | Trp | Glu | Ile | Phe | Thr | Leu | Gly |
|  |  | 595 |  |  |  |  | 600 |  |  |  |  | 605 |  |  |  |
| Gly | Ser | Pro | Tyr | Pro | Gly | Val | Pro | Val | Glu | Glu | Leu | Phe | Lys | Leu | Leu |
|  | 610 |  |  |  |  | 615 |  |  |  |  | 620 |  |  |  |  |
| Lys | Glu | Gly | His | Arg | Met | Asp | Lys | Pro | Ser | Asn | Cys | Thr | Asn | Glu | Leu |
| 625 |  |  |  |  | 630 |  |  |  |  | 635 |  |  |  |  | 640 |
| Tyr | Met | Met | Met | Arg | Asp | Cys | Trp | His | Ala | Val | Pro | Ser | Gln | Arg | Pro |
|  |  |  |  | 645 |  |  |  |  | 650 |  |  |  |  | 655 |  |
| Thr | Phe | Lys | Gln | Leu | Val | Glu | Asp | Leu | Asp | Arg | Ile | Val | Ala | Leu | Thr |
|  |  |  | 660 |  |  |  |  | 665 |  |  |  |  | 670 |  |  |
| Ser | Asn | Gln | Glu | Tyr | Leu | Asp | Leu | Ser | Met | Pro | Leu | Asp | Gln | Tyr | Ser |
|  |  | 675 |  |  |  |  | 680 |  |  |  |  | 685 |  |  |  |
| Pro | Ser | Phe | Pro | Asp | Thr | Arg | Ser | Ser | Thr | Cys | Ser | Ser | Gly | Glu | Asp |
|  | 690 |  |  |  |  | 695 |  |  |  |  | 700 |  |  |  |  |
| Ser | Val | Phe | Ser | His | Glu | Pro | Leu | Pro | Glu | Glu | Pro | Cys | Leu | Pro | Arg |
| 705 |  |  |  |  | 710 |  |  |  |  | 715 |  |  |  |  | 720 |
| His | Pro | Ala | Gln | Leu | Ala | Asn | Gly | Gly | Leu | Lys | Arg | Arg |  |  |  |
|  |  |  |  | 725 |  |  |  |  | 730 |  |  |  |  |  |  |

( 2 ) INFORMATION FOR SEQ ID NO:5:

( i ) SEQUENCE CHARACTERISTICS:
        ( A ) LENGTH: 300 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

| Met | Trp | Ser | Trp | Lys | Cys | Leu | Leu | Phe | Trp | Ala | Val | Leu | Val | Thr | Ala |
|---|---|---|---|---|---|---|---|---|---|---|---|---|---|---|---|
| 1 |  |  |  | 5 |  |  |  |  | 10 |  |  |  |  | 15 |  |
| Thr | Leu | Cys | Thr | Ala | Arg | Pro | Ser | Pro | Thr | Leu | Pro | Glu | Gln | Asp | Ala |
|  |  |  | 20 |  |  |  |  | 25 |  |  |  |  | 30 |  |  |
| Leu | Pro | Ser | Ser | Glu | Asp | Asp | Asp | Asp | Asp | Asp | Ser | Ser | Ser | Ser | Glu |
|  |  | 35 |  |  |  |  | 40 |  |  |  |  | 45 |  |  |  |
| Glu | Lys | Glu | Thr | Asp | Asn | Thr | Lys | Pro | Asn | Pro | Val | Ala | Pro | Tyr | Trp |
|  | 50 |  |  |  |  | 55 |  |  |  |  | 60 |  |  |  |  |
| Thr | Ser | Pro | Glu | Lys | Met | Glu | Lys | Lys | Leu | His | Ala | Val | Pro | Ala | Ala |
| 65 |  |  |  |  | 70 |  |  |  |  | 75 |  |  |  |  | 80 |
| Lys | Thr | Val | Lys | Phe | Lys | Cys | Pro | Ser | Ser | Gly | Thr | Pro | Asn | Pro | Thr |
|  |  |  |  | 85 |  |  |  |  | 90 |  |  |  |  | 95 |  |
| Leu | Arg | Trp | Leu | Lys | Asn | Gly | Lys | Glu | Phe | Lys | Pro | Asp | His | Arg | Ile |
|  |  |  | 100 |  |  |  |  | 105 |  |  |  |  | 110 |  |  |
| Gly | Gly | Tyr | Lys | Val | Arg | Tyr | Ala | Thr | Trp | Ser | Ile | Ile | Met | Asp | Ser |
|  |  | 115 |  |  |  |  | 120 |  |  |  |  | 125 |  |  |  |
| Val | Val | Pro | Ser | Asp | Lys | Gly | Asn | Tyr | Thr | Cys | Ile | Val | Glu | Asn | Glu |
|  | 130 |  |  |  |  | 135 |  |  |  |  | 140 |  |  |  |  |
| Tyr | Gly | Ser | Ile | Asn | His | Thr | Tyr | Gln | Leu | Asp | Val | Val | Glu | Arg | Ser |

|     |     |     |     | 145 |     |     |     |     | 150 |     |     |     |     | 155 |     |     |     |     | 160 |
|-----|-----|-----|-----|-----|-----|-----|-----|-----|-----|-----|-----|-----|-----|-----|-----|-----|-----|-----|-----|

Pro His Arg Pro Ile Leu Gln Ala Gly Leu Pro Ala Asn Lys Thr Val
            165                 170                 175

Ala Leu Gly Ser Asn Val Glu Phe Met Cys Lys Val Tyr Ser Asp Pro
            180                 185                 190

Gln Pro His Ile Gln Trp Leu Lys His Ile Glu Val Asn Gly Ser Lys
            195                 200                 205

Ile Gly Pro Asp Asn Leu Pro Tyr Val Gln Ile Leu Lys Val Ile Met
    210                 215                 220

Ala Pro Val Phe Val Gly Gln Ser Thr Gly Lys Glu Thr Thr Val Ser
225                 230                 235                 240

Gly Ala Gln Val Pro Val Gly Arg Leu Ser Cys Pro Arg Met Gly Ser
                245                 250                 255

Phe Leu Thr Leu Gln Ala His Thr Leu His Leu Ser Arg Asp Leu Ala
            260                 265                 270

Thr Ser Pro Arg Thr Ser Asn Arg Gly His Lys Val Glu Val Ser Trp
            275                 280                 285

Glu Gln Arg Ala Ala Gly Met Gly Gly Ala Gly Leu
            290                 295                 300

( 2 ) INFORMATION FOR SEQ ID NO:6:

( i ) SEQUENCE CHARACTERISTICS:
         ( A ) LENGTH: 302 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO:6:

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Asp Ala
            20                  25                  30

Leu Pro Ser Ser Glu Asp Asp Asp Asp Asp Asp Ser Ser Ser Glu
            35                  40                  45

Glu Lys Glu Thr Asp Asn Thr Lys Pro Asn Arg Met Pro Val Ala Pro
    50                  55                  60

Tyr Trp Thr Ser Pro Glu Lys Met Glu Lys Lys Leu His Ala Val Pro
65                  70                  75                  80

Ala Ala Lys Thr Val Lys Phe Lys Cys Pro Ser Ser Gly Thr Pro Asn
                85                  90                  95

Pro Thr Leu Arg Trp Leu Lys Asn Gly Lys Glu Phe Lys Pro Asp His
            100                 105                 110

Arg Ile Gly Gly Tyr Lys Val Arg Tyr Ala Thr Trp Ser Ile Ile Met
            115                 120                 125

Asp Ser Val Val Pro Ser Asp Lys Gly Asn Tyr Thr Cys Ile Val Glu
    130                 135                 140

Asn Glu Tyr Gly Ser Ile Asn His Thr Tyr Gln Leu Asp Val Val Glu
145                 150                 155                 160

Arg Ser Pro His Arg Pro Ile Leu Gln Ala Gly Leu Pro Ala Asn Lys
                165                 170                 175

Thr Val Ala Leu Gly Ser Asn Val Glu Phe Met Cys Lys Val Tyr Ser
            180                 185                 190

Asp Pro Gln Pro His Ile Gln Trp Leu Lys His Ile Glu Val Asn Gly
            195                 200                 205

Ser Lys Ile Gly Pro Asp Asn Leu Pro Tyr Val Gln Ile Leu Lys Val

```
                    210                         215                              220
        Ile  Met  Ala  Pro  Val  Phe  Val  Gly  Gln  Ser  Thr  Gly  Lys  Glu  Thr  Thr
        225                      230                      235                           240

Val  Ser  Gly  Ala  Gln  Val  Pro  Val  Gly  Arg  Leu  Ser  Cys  Pro  Arg  Met
                           245                           250                      255

Gly  Ser  Phe  Leu  Thr  Leu  Gln  Ala  His  Thr  Leu  His  Leu  Ser  Arg  Asp
                      260                      265                           270

Leu  Ala  Thr  Ser  Pro  Arg  Thr  Ser  Asn  Arg  Gly  His  Lys  Val  Glu  Val
                 275                           280                      285

Ser  Trp  Glu  Gln  Arg  Ala  Ala  Gly  Met  Gly  Gly  Ala  Gly  Leu
             290                      295                      300
```

( 2 ) INFORMATION FOR SEQ ID NO:7:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

```
CCATTTGTCG ACTTCCATCT TTTCTGGGGA TGTCCA                                          36
```

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

```
GCGGCGTTTG AGTCCGCCAT TGGCAAGCTG                                                 30
```

( 2 ) INFORMATION FOR SEQ ID NO:9:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
CCAACCTCTA GAGGATCCAC TGGGATGTGG AGCTGGAAGT GC                                   42
```

( 2 ) INFORMATION FOR SEQ ID NO:10:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

```
GTAAGCGGCC GCGGATCCTT ACTACTCCAG GTACAGGGGC GA                                   42
```

( 2 ) INFORMATION FOR SEQ ID NO:11:

( i ) SEQUENCE CHARACTERISTICS:
        ( A ) LENGTH: 36 base pairs

-continued (B) TYPE: nucleic acid
(C) STRANDEDNESS: single
(D) TOPOLOGY: linear ( i i ) MOLECULE TYPE: cDNA ( x i ) SEQUENCE DESCRIPTION: SEQ ID NO:11:

CCATTTGGAT CCGTCACAGC CACACTCTGC ACCGCT  36

( 2 ) INFORMATION FOR SEQ ID NO:12:

(i) SEQUENCE CHARACTERISTICS:
(A) LENGTH: 36 base pairs
(B) TYPE: nucleic acid
(C) STRANDEDNESS: single
(D) TOPOLOGY: linear ( i i ) MOLECULE TYPE: cDNA ( x i ) SEQUENCE DESCRIPTION: SEQ ID NO:12:

CCATTTGTCG ACTTCCATCT TTCTGGGGA TGTCCA  36